(12) United States Patent
Van Lankvelt et al.

(10) Patent No.: US 8,237,434 B2
(45) Date of Patent: Aug. 7, 2012

(54) ELECTROMAGNETIC SYSTEM FOR BIOSENSORS

(75) Inventors: Petrus Johannes Wilhelmus Van Lankvelt, Boekel (NL); Menno Willem Jose Prins, Rosmalen (NL); Albert Hendrik Jan Immink, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 416 days.

(21) Appl. No.: 12/528,844

(22) PCT Filed: Feb. 29, 2008

(86) PCT No.: PCT/IB2008/050740
§ 371 (c)(1),
(2), (4) Date: Aug. 27, 2009

(87) PCT Pub. No.: WO2008/107827
PCT Pub. Date: Sep. 12, 2008

(65) Prior Publication Data
US 2010/0117772 A1    May 13, 2010

(30) Foreign Application Priority Data
Mar. 6, 2007  (EP) .................................... 07103629

(51) Int. Cl.
G01N 27/72    (2006.01)
G01N 27/74    (2006.01)
G01N 27/82    (2006.01)

(52) U.S. Cl. ......... 324/239; 324/204; 324/240; 324/244
(58) Field of Classification Search ................ 324/239, 324/204, 240, 244.1; 335/219
See application file for complete search history.

(56) References Cited

U.S. PATENT DOCUMENTS 3,569,698 A * 3/1971 Herrman .................... 250/398
6,858,433 B1 * 2/2005 Zivitz ........................ 436/151
2007/0116600 A1 * 5/2007 Kochar et al. .............. 422/65

FOREIGN PATENT DOCUMENTS
DE    10137665 A1    11/2002
WO    0140790 A1    6/2001

OTHER PUBLICATIONS

Luxton et al: "Use of External Magnetic Fields to Reduce Reaction Times in an Immunoassay Using Micrometer-Sized Paramagnetic Particles as Labels (Magnetoimmunoassay)"; Analytical Chemistry, vol. 76, No. 6, Mar. 15, 2004, pp. 1715-1719.
Edelstein et al: "The BARC Biosensor Applied to the Detection of Biological Warfare Agents": Biosensors & Bioelectronics, vol. 14 (2000), pp. 805-813.

* cited by examiner

Primary Examiner — M'Baye Diao

(57) ABSTRACT

An electromagnetic system for biosensors including two independent electromagnetic units separated in the region of pole shoes of the electromagnetic units positioned under a gap, a cartridge positioned in the gap providing a sample volume and a biosensor having a sensor surface located at one or more inner surfaces of the cartridge proximate to the pole shoes.

12 Claims, 2 Drawing Sheets

ELECTROMAGNETIC SYSTEM FOR BIOSENSORS

FIELD OF THE INVENTION

Figures 1A, 1B:
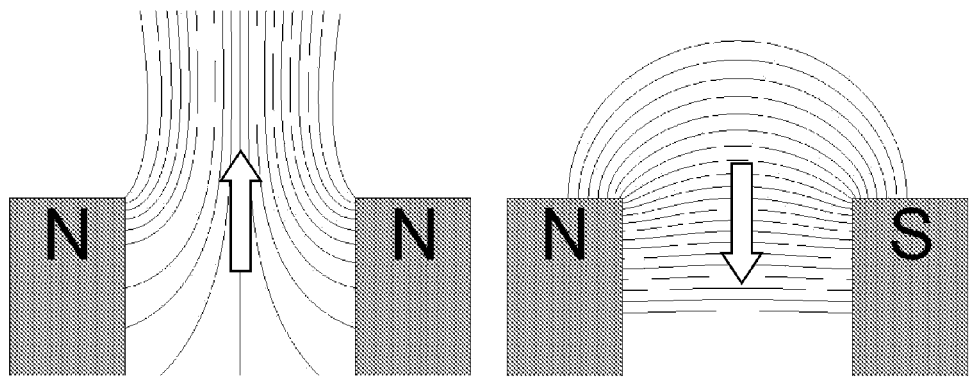

The invention relates to an electromagnetic system for a biosensor.

BACKGROUND OF THE INVENTION

Electromagnetic systems for biosensors are used in combination with magnetic beads, which commonly are solved in the biomaterial to be analysed.

This use of magnetic labels in biosensors has several advantages. One can actuate the beads by applying a magnetic field gradient. This allows to control the assay, to speed up the procedure, and to make the assay more specific and more reliable.

Furthermore, no magnetic background signal is present from biological fluids, which is an advantage when the labels are detected by magnetic means.

Magnetic labels can be detected by various means, e.g. the sensor or biosensor can be any suitable sensor to detect the presence of magnetic particles on or near to a sensor surface, based on any property of the particles, e.g. it can detect via magnetic methods, e.g. magneto-resistive methods, hall-sensors, coils, optical methods, imaging, fluorescence, chemiluminescence, absorption, scattering, surface plasmon resonance, Raman, sonic detection, e.g. surface-acoustic-wave, bulk acoustic wave, cantilever, quartz crystal etc, electrical detection, e.g. conduction, impedance, amperometric, redox cycling, etc.

The challenge is to design a magnetic system with the following properties:
 high switchable gradient
 magnet on only one side of the cartridge
 no mechanical movement needed to achieve switching of the magnetic field
 self-alignment of the cartridge in the reader, i.e. alignment of the sensor surface with respect to the maximum force region of the magnet.

The actuation of magnetic labels requires a switchable field gradient, for forces toward and forces away from the sensor surface. These forces are needed for up-concentration of labels near to the sensor surface and for magnetic stringency, for example. A known solution is to take two magnets on either side of the cartridge [e.g. Luxton, Anal. Chem. 76, 1715 (2004)]. A disadvantage of this solution is that geometrical constraints exist for the cartridge and also for the sensor read-head, and it involves a high number of parts.

SUMMARY OF THE INVENTION

It is an object of the present invention to achieve an electromagnetic system for biosensors, in which the system can switch quickly between high magnetic gradients, without the need of movement of mechanical elements.

The stated object is achieved for an electromagnetic system for biosensors by the features of patent claim 1.

Disclosed is a biosensor magnet with two magnetic subunits that are separated by a gap, characterized in that the magnetic field gradient at the sensor surface can be switched by electrical control of the relative orientation of the magnetizations of the two respective subunits.

Further embodiments of the invention are characterized in the dependant claims 2-9.

The basic idea and function of the invention are, that two independent electromagnetic units are separated in the region of the pole shoes over a gap, in which a sample volume is arranged by a cartridge, in which the sensor surfaces are located on one or more inner surfaces of the cartridge.

Advantages of this solution are:
 high switch-able field gradient without mechanical movement
 the magnet is positioned on only one side of the cartridge, making the system suitable for several detection techniques (e.g. optical, magnetic)
 simple sliding movement gives good alignment of sensor surface with respect to the magnet.

An embodiment is characterized in that the electromagnetic units are arranged in parallel, so that the magnetic cores extend over at least the height of the cartridge out of the upper end of the magnetic units, and the cartridge is arranged between these parallel arranged extending magnetic core parts in a slit. So the cartridge, and with this the fluids come in the nearest possible influence of the magnet field-lines.

In a further embodiment of the invention the electromagnetic units are driven or steered by electric means in that way, that the magnetic polarisation between the magnetic core parts can be switched between N-N, N-S, S-N and S-S. By this means the magnetic force to the fluid can be switched easily and quickly between effective repulsion and attraction.

A further embodiment of the invention is that the open side of the cartridge is covered with an optical window.

By this also in further embodiment focussing optical read-out means can arranged above the optical windows. Also, the analyte, which means the substance to be detected by the biosensor, can be realized automatically by electronic signal evaluation.

In a further embodiment the cartridge has a U-profile and is made of at least nearly non-susceptible material. Such a cartridge form can be designed straightforward in the given constructive gap between the magnetic core elements, and can easily be covered by the aforesaid window. It results in a closed tube-formed cartridge, through which the fluid media can effectively be passed through.

For the effective use of surfaces for localizing the active sensors or sensor surfaces, one sensor or sensor surface is located at the bottom of the cartridge and the other is located adjacent to this, and the readout system is a magnetic readout system.

To summarize, the cartridge is a sample-flow-channel, where fluids to be analysed are pumped or sucked through.

DRAWINGS

Different embodiments of the invention are shown in FIG. 1 to FIG. 4.

FIG. 1 schematic drawing of the two different magnetic orientations

Figure 2:
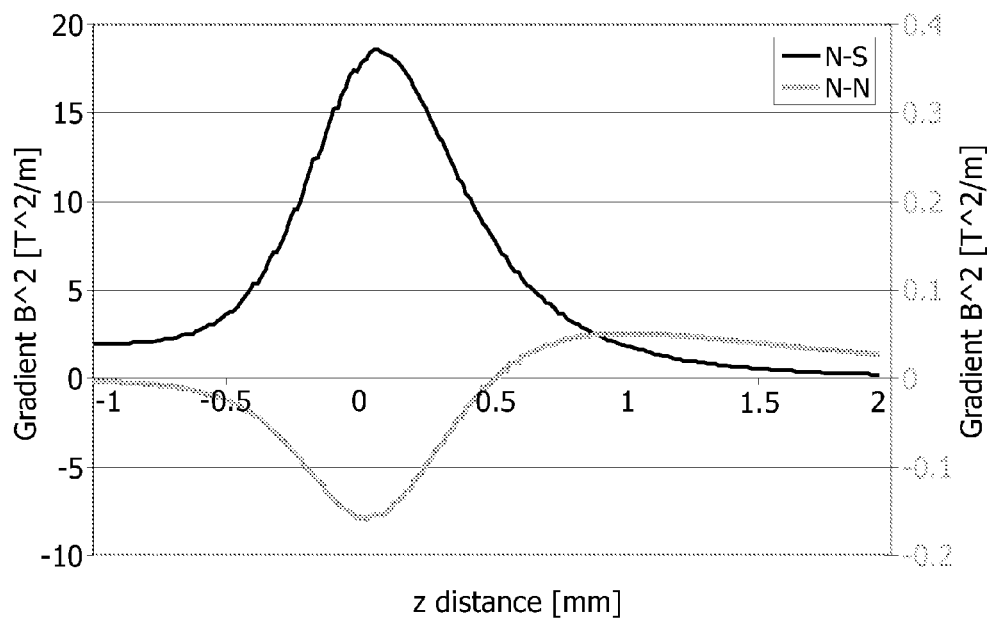

FIG. 2 calculation of the gradient of $B^2$ dependant on the distance z

Figure 3:
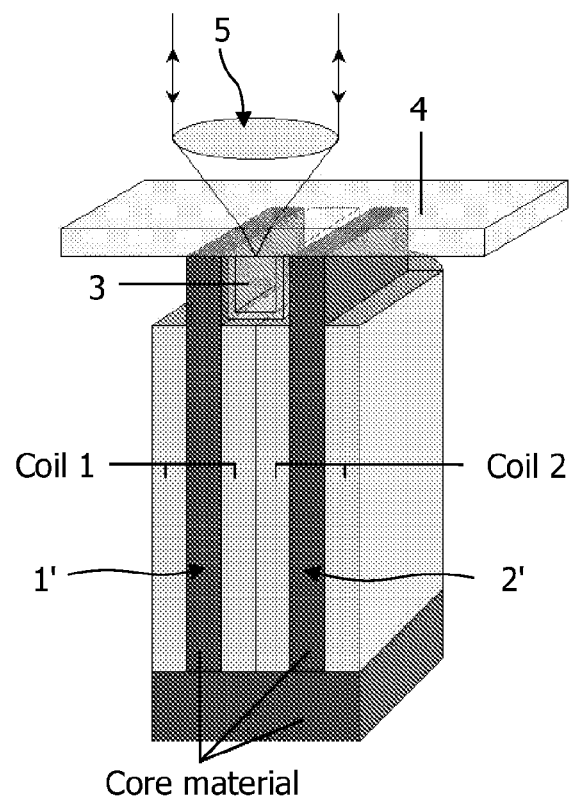

FIG. 3 embodiment with optical reader

Figure 4:
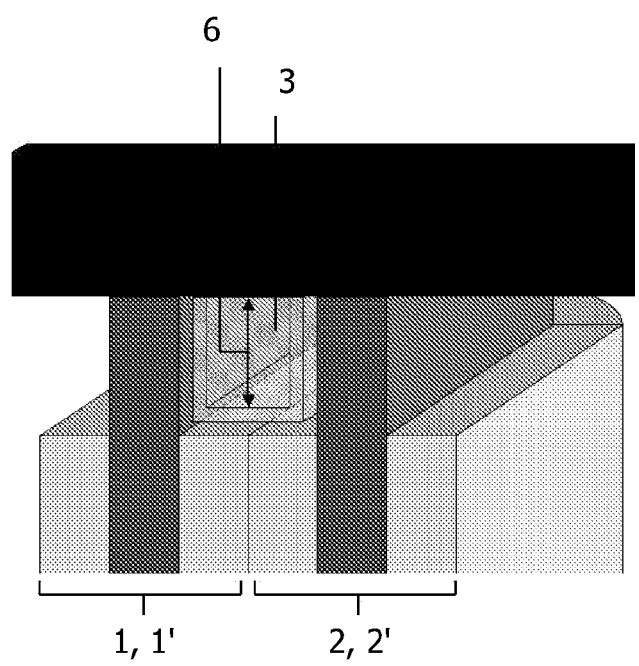

FIG. 4 embodiment with cartridge

A first schematic drawing of the detailed part of the magnetic system is shown in FIG. 1. By this, two separately controllable magnetic subunits are given, so that the orientation of the magnetization of both units can be chosen independent of each other, which is shown in this FIG. 1. By this quality the system can have two different configurations, namely North-North and North-South (South-South results in the same configuration as North-North). The magnetic forces of both configurations are schematically shown in FIG.

2. The magnetic field pattern of both configurations is changed in a way, that the highest magnetic flux density is moved from somewhere above the slit to somewhere inside the slit. This means that in the region of interest (between and just above the slit) the gradient (~force) has been changed in sign. In other words: by changing the polarity of one of the two magnetic subunits the direction of the force is flipped.

Only the upper parts of the subunits are drawn together with a few magnetic field lines in the region of interest. (a) Both subunits have the same magnetization orientation (N-N). (b) The subunits have opposite orientation with respect to each other (N-S). The magnetic field pattern of both configurations has changed in a way that the gradient (~force) of the magnetic field has flipped, which is indicated by the arrow.

Magnetic field gradient calculations of both configurations as described in this embodiment are shown in FIG. 2. The magnetic force applied on a magnetic particle is proportional to the gradient of $B^2$, which means that the curves shown in FIG. 2 are proportional to the force applied by the system for the two different configurations. A change in sign means a change in force direction. This proves that the described magnetic system can switch in magnetic force direction by simply changing electrically the magnetization of one of the two subunits.

FIG. 2 therefore shows calculations of the gradient of $B^2$, which are induced by the two different pole configurations. The calculations are performed in the middle of the two magnetic subunits. At the pole surfaces, the z distance is defined as zero. Further downwards (between the subunits/inside the slit) the z value becomes negative and above the pole surfaces, the z is defined as positive. A positive gradient means that the force is directed downwards like in FIG. 1b. A negative gradient means that the force is directed upwards like in FIG. 1a. Note that both curves have different values at y-axis.

An advantageous embodiment is shown in FIG. 3. In this embodiment, it is sketched one possible use of the magnetic system in combination with an optical detection system.

Optical labels offer some desirable properties:
Many detection possibilities like imaging, fluorescence, absorption, scattering, turbidometry, SPR, SERRS, luminescence, chemiluminescence, electrochemiluminescence, FRET, etc.
Imaging possibility offers high multiplexing.
Optical labels are generally small and do not influence the assay too much.

A good combination would be to use magnetic labels that can be actuated by applying magnetic field gradients and that can be detected optically. In this case the optical detection can be done automatically by optic-sensor means.

Advantageous is, that optics and magnetics are orthogonal in the sense, that in most cases, optical beams do not show interference with magnetic fields and vice versa. This means that magnetic actuation would be ideally suited for combination with optical detection. Problems such as sensor disturbance by the actuation fields are eliminated.

The problem of combining magnetic actuation and optical detection is in the geometrical constraint. To develop a cartridge technology that is compatible with magnetic actuation means, typically an electromagnet needs to operate at a small distance between magnet and sensor surface. An optical system needs to scan the same surface, possible with high-NA (numerical aperture) optics.

The optic-mechanical set-up and the electromagnet therefore hinder each other when integrating a concept with magnetic actuation and optical detection. Preferably, a configuration with a magnet on only one side is needed. This magnet should be able to generate a switch-able magnetic field. In an embodiment the switching of the magnetic field gradient in this configuration is done without any mechanical movement.

This embodiment therefore describes an advantageous construction for a compact optical biosensor system, which consists of the magnetic slit system 1, 2, 1', 2' in combination with an optical detection/readout system 5.

Two magnetic subunits consist of a first coil 1 with a first core 1', and a second coil 2 with a second core 2'. These subunits are arranged in parallel. The cores 1' and 2' have a rectangular cross section. The out-coming cores 1' and 2' constructively cause a slit.

The dual force quality of the magnetic system makes it possible to use an optical detection system 5 on the other side. This configuration has a flow channel or a cartridge 3, containing the sample volume, which is placed in this slit, where the active surface is aligned with the pole surfaces of both magnetic subunits. The sample volume is now placed in the region of interest where the direction of the magnetic force can be switched and the active/sensor surface is at the maximum force region (z=0, see FIG. 2). Through an optical window 4, the sensor surface can be scanned without scanning through the noisy sample volume.

FIG. 4 shows a last embodiment with some detailed functions realized. In this embodiment another possible use of the magnetic system is shown, namely the combination with a magnetic detection chip.

This embodiment describes a magnetic biosensor system, which consists of the magnetic slit system in combination with a magnetic detection and readout system 6. By this we use the benefits of the slit system, which are easy and good alignment of the cartridge and maximal magnetic force at the sensor surface without any mechanical movements.

In this embodiment a flow channel or cartridge 3 as well, containing the sample volume is placed in the slit where the active surface is aligned with the pole surfaces of both magnetic subunits. Without the needs of an optical window we have more freedom in choosing of the place of the sensor active surfaces 6, which are a magnetic readout. Another benefit of this slit system is that directions of the magnetic fields are more homogeneous over the slit compared to an axial symmetrical system. Independent of the alignment of the sensor, for instance GMRs (Giant Magneto Resistive sensor) with respect to the slit, the magnetic field direction with respect to the slit is always the same.

The fluid to be analyzed is sucked or pumped through the cartridge 3 by pumping or sucking means which have to be applied at one end of the cartridge 3.

Several advantages can be realized by this:
No mechanical moving parts to switch from repelling force to attractive force.
Simple sliding movement gives good alignment
Suitable for optical sensing, magnetic sensing, etc.
Further effects:
In addition to molecular assays, also larger moieties can be detected, e.g. cells, viruses, or fractions of cells or viruses, tissue extract, etc.

The detection can occur with or without scanning of the sensor element with respect to the biosensor surface.

Measurement data can be derived as an end-point measurement, as well as by recording signals kinetically or intermittently.

The labels can be detected directly by the sensing method. As well, the particles can be further processed prior to detection. An example of further processing is that materials are added, or that the (bio) chemical or physical properties of the label are modified to facilitate detection.

The device can be used with several biochemical assay types, e.g. binding/unbinding assay, sandwich assay, competition assay, displacement assay, enzymatic assay, etc.

The device and systems of this invention are suited for sensor multiplexing (i.e. the parallel use of different sensors and sensor surfaces), label multiplexing (i.e. the parallel use of different types of labels) and chamber multiplexing (i.e. the parallel use of different reaction chambers).

The device and systems described in the present invention can be used as rapid, robust, and easy to use point-of-care biosensors for small sample volumes. The reaction chamber can be a disposable item to be used with a compact reader, containing the one or more magnetic field generating means and one or more detection means.

Also, the device and systems of the present invention can be used in automated high-throughput testing. In this case, the reaction chamber is e.g. a well plate or cuvette, fitting into an automated instrument.

REFERENCE NUMBERS 1 first coil
2 second coil
1' first core
2' second core
3 Cartridge
4 Optical window
5 Optical system reader, optical readout system
6 Sensor surfaces, magnetic readout system

The invention claimed is:

1. An electromagnetic system for biosensors, the system comprising:
   two independent electromagnetic units separated in the region of pole shoes of the electromagnetic units positioned under a gap;
   a cartridge positioned in the gap providing a sample volume; and
   a biosensor having a sensor surface located at one or more inner surfaces of the cartridge proximate to the pole shoes.

2. The electromagnetic system according to claim 1, wherein the electromagnetic units are arranged in parallel with corresponding magnetic cores extending over at least a height of the cartridge out of an upper end of the magnetic units, the cartridge arranged between these parallel arranged extending magnetic core parts in the gap.

3. The electromagnetic system according to claim 1, wherein the electromagnetic units are each individually driven or steered by an electric signal enabling switching between N-N, N-S, S-N and S-S polarizations.

4. The electromagnetic system according to claim 1, comprising an optical window, an open side of the cartridge covered with the optical window.

5. The electromagnetic system according to claim 4, comprising an optical sensor arranged above the optical window.

6. The electromagnetic system according to claim 4, wherein the cartridge has a U-profile and is made of at least nearly non-susceptible material.

7. The electromagnetic system according to claim 1, the system comprising a magnetic sensor positioned above the gap, wherein the biosensor is located at a bottom of the cartridge adjacent to the sensor surface.

8. The electromagnetic system according to claim 1, wherein the cartridge comprises a sample-flow-channel, where fluids to be analyzed are pumped or sucked through.

9. The electromagnetic system according to claim 1, comprising an optical window positioned over the cartridge and an optoelectronic sensor arranged in at a focus of the optical window.

10. An electromagnetic system for biosensors, comprising:
    two independent electromagnetic units separated in the region of pole shoes of the electromagnetic units over a gap,
    a cartridge in which a sample volume is arranged, and
    a biosensor located at one or more inner surfaces of the cartridge, wherein the electromagnetic units are arranged in parallel with corresponding magnetic cores extending over at least a height of the cartridge out of an upper end of the magnetic units, the cartridge arranged between these parallel arranged extending magnetic core parts in the gap.

11. An electromagnetic system for biosensors, the system comprising:
    two independent electromagnetic units separated in the region of pole shoes of the electromagnetic units positioned under a gap;
    a cartridge positioned in the gap providing a sample volume; and
    a biosensor having a sensor surface located on an inner surface of the cartridge, wherein a position of the two independent electromagnetic units is fixed in relation to the cartridge and the electromagnetic units are each individually driven or steered by an electric signal enabling switching between N-N, N-S, S-N and S-S polarizations.

12. The electromagnetic system according to claim 11, wherein the electromagnetic units are arranged in parallel with corresponding magnetic cores extending over at least a height of the cartridge out of an upper end of the magnetic units, the cartridge arranged between these parallel arranged extending magnetic core parts in the gap.

* * * * *